US00PP20813P2

(12) United States Plant Patent
Jandrew

(10) Patent No.: US PP20,813 P2
(45) Date of Patent: Mar. 9, 2010

(54) *IPOMOEA* PLANT NAMED 'SEKI BLAHRT'

(50) Latin Name: *Ipomoea batatas (L.) Lam*
Varietal Denomination: Seki Blahrt

(75) Inventor: Jason Jandrew, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/316,300

(22) Filed: Dec. 11, 2008

(51) Int. Cl.
*A01H 5/00* (2006.01)

(52) U.S. Cl. ..... Plt./263.1

(58) Field of Classification Search ..... Plt./258, Plt./263.1
See application file for complete search history.

*Primary Examiner*—Kent L Bell
(74) *Attorney, Agent, or Firm*—S. Matthew Edwards

(57) ABSTRACT

A new *Ipomoea* plant named 'Seki Blahrt' particularly distinguished by compact and mounding plant habit, then becomes more outwardly trailing with age, vigorous, freely branching with dense foliage, and very dark, almost black, cordate or 'heart' shaped foliage, with soft pink and white flowers.

1 Drawing Sheet

Latin name of the genus and species of the plant claimed: *Ipomoea batatas* (*L.*) *Lam.*

Varietal denomination: 'Seki Blahrt'.

BACKGROUND OF THE NEW PLANT

The present invention comprises a new *Ipomoea*, botanically known as *Ipomoea batatas* (*L.*) *Lam*, and commonly known as Ornamental Sweet Potato, and hereinafter referred to by the variety name 'Seki Blahrt.' These plants are grown, not for their flowers, but for their foliage and plant habit characteristics. These plants flower very rarely and then only under strict short day lengths. Each flower is ephemeral, in that it only lasts up to 24 hours, and blooms mostly through the night and early morning hours.

'Seki Blahrt' is a product of a planned breeding program. The new cultivar 'Seki Blahrt' has compact and mounding plant habit, then becomes more outwardly trailing with age, vigorous, freely branching with dense foliage, and very dark, almost black, cordate or 'heart' shaped foliage, with soft pink and white flowers.

'Seki Blahrt' originated from a hybrid cross in a controlled breeding program in Gilroy, Calif. USA. The female parent was 'Sweet Caroline Purple' (U.S. Plant Pat. No. 14,912). 'Sweet Caroline Purple' has a less compact plant habit, larger and lighter colored palmate foliage than 'Seki Blahrt.'

The male parent of 'Seki Blahrt' was 'Sweet Caroline Sweetheart Purple' (U.S. Plant Pat. No. 18,573). 'Sweet Carolina Sweetheart Purple' has a less compact plant habit, lighter colored leaves and stems than 'Seki Blahrt.'

'Seki Blahrt' was selected as one flowering plant within the progeny of the stated cross in March 2007, in a controlled environment in Gilroy, Calif. USA.

The pollination took place in October 2006 and the seed sown in December 2006. The first act of asexual reproduction of 'Seki Blahrt' was accomplished when vegetative cuttings were taken from the initial selection in the March 2007 in a controlled environment in Gilroy, Calif. USA.

Horticultural examination of plants grown from cuttings of the plant initiated in March 2007 in Gilroy, Calif. USA, and continuing thereafter, has demonstrated that the combination of characteristics as herein disclosed for 'Seki Blahrt' are firmly fixed and are retained through successive generations of asexual reproduction.

'Seki Blahrt' has not been observed under all possible environmental conditions. The phenotype may vary significantly with variations in environment such as temperature, light intensity and day length.

A Plant Breeder's Right for this cultivar was applied for in Canada on Dec. 24, 2007. 'Seki Blahrt' has not been made publicly available more than one year prior to the filing of this application.

DESCRIPTION OF DRAWING

The accompanying photographic drawing shows typical foliage and plant habit characteristics of 'Seki Blahrt' with colors being as true as possible with an illustration of this type. The photographic drawing shows 3 potted plants of the new variety growing in a 14 inch container. These plants were grown and photographed in Gilroy, Calif. USA in the summer of 2008.

DETAILED BOTANICAL DESCRIPTION

The measurements were taken in October 2008 in Gilroy, Calif. USA on plants that were growing in 6 inch pots in a greenhouse. Culture of these plants started in about August 2008, when they came from sterile tissue culture tubes after laboratory micropropagation.

Color Chart used: Royal Horticultural Society Colour Chart (R.H.S.) 2001

BRIEF SUMMARY OF INVENTION

The following observations, measurements, and comparisons describe plants grown in Gilroy, Calif. USA. The following traits have been repeatedly observed and are determined to be basic characteristics of the new variety. The combination of these characteristics distinguishes this *Ipomoea* as a new and distinct variety.

TABLE 1

DIFFERENCES BETWEEN THE NEW VARIETY 'SEKI BLAHRT' AND A SIMILAR VARIETY

| | 'Seki Blahrt' | 'Sweet Caroline Sweetheart Purple' (U.S. Plant Pat. No. 18,573) |
|---|---|---|
| Petiole size/color | Shorter/RHS 187A to RHS 187B | Longer/RHS 187A |
| Leaf size | Smaller | Larger |
| Stems color | RHS N186C | RHS 183A |
| Peduncle color | RHS 183B | RHS 59A |

Plant:

*Form, growth and habit.*—Compact and mounding plant habit that becomes more outwardly trailing with age, vigorous, freely branching with dense foliage.

*Height.*—22–25 cm.

*Width.*—45–50 cm.

Roots/tubers:

*Type.*—At the age of these plants used for the descriptive data, there were no real tubers forming. The roots themselves are thick, fleshy and cream to white.

Foliage:

*Type.*—Alternate, simple.

*Immature, leaf color, upper surface.*—RHS 144A, quickly becoming heavily overlaid with a light RHS 166A; RHS 144B veins.

*Lower surface.*—Closest to RHS 146B; RHS 144B veins.

*Mature, leaf color, upper surface.*—RHS N189A ground color overlaid with anthocyanins of between RHS N186B and RHS N186C.

*Lower surface.*—Approximately the same as the upper surface.

*Length.*—9.5–11 cm.

*Width.*—6.7–7.4 cm.

*Shape.*—Cordate.

*Base shape.*—Cordate.

*Apex shape.*—Apiculate to almost aristate.

*Margin.*—Entire.

*Texture.*—Hirsute on the margins of both surfaces.

*Color of veins, upper surface.*—Closest to RHS186C.

*Color of veins, lower surface.*—Closest to RHS186C.

*Petioles color.*—RHS 187A to RHS 187B.

*Petioles length.*—12–14 cm.

*Diameter of petiole.*—0.3 cm.

*Texture.*—Glabrous.

Stem:

*Color of stem.*—RHS N186C.

*Length of stem.*—25–30 cm.

*Diameter.*—0.3–0.5 cm.

*Length of internodes.*—0.5–1.0 cm.

*Texture.*—Glabrous.

Inflorescence:

*Type.*—Ephemeral; rarely see flowers. Flowers only under very strict short day lengths.

*Fragrance.*—None.

*Color of peduncle.*—RHS 183B.

*Length of peduncle.*—0.3 cm.

*Peduncle diameter.*—0.2 cm.

*Texture.*—Glabrous.

Corolla:

*Form.*—Single trumpet-shaped flowers arise from leaf axils comprised of 5 petals fused at the corolla length and base.

*Flower diameter.*—3.6–3.8 cm.

*Flower depth.*—3.5 cm.

*Color of petals, upper surface.*—RHS 76C ground color; RHS 76B at the margins.

*Color of petals, lower surface.*—RHS 76 B to C; RHS 77D veins.

*Length of petals.*—1.2–1.3 cm.

*Width of petals.*—1.0–1.1 cm.

*Petal shape.*—Obcordate.

*Apex shape.*—Rounded to broadly obtuse.

*Margin.*—Entire.

*Petal texture.*—Papillose on upper surface and glabrous on under surface.

*Corolla color inner surface.*—RHS 77B; RHS 77A veins.

*Outer surface.*—RHS 77C but greyer.

*Corolla diameter at flare.*—1.5 cm.

Bud (just before opening):

*Color.*—RHS 76B to C.

*Length.*—1.9–2.1 cm.

*Width.*—0.5–0.7 cm.

*Shape.*—Orbicular.

*Calyx.*—5 sepals fused at the base.

*Color of sepals, inner surface.*—RHS N186A to B.

*Outer surface.*—Closest to RHS N186A.

*Length of sepals.*—1.0–1.1 cm.

*Width of sepals.*—0.2–0.3 cm.

*Sepal shape.*—Lanceolate.

*Apex shape.*—Acute.

*Margins.*—Entire.

*Texture.*—Slightly pubescent on the outer surface and glabrous on the inner surface.

Reproductive organs:

*Pistil.*—1.

*Length.*—1.6 cm.

*Style color.*—RHS N155B but whiter.

*Style length.*—1.4 cm.

*Stigma color.*—RHS N155B but whiter.

*Stamens.*—5.

*Color of filaments.*—RHS N155B but whiter.

*Length filaments.*—0.6–0.7 cm.

*Anther color.*—RHS 155C.

*Length of anthers.*—0.2 cm.

*Color of pollen.*—RHS 155A.

*Pollen amount.*—Scarce.

*Fertility/seed set.*—Not observed on this hybrid.

Disease/pest resistance: Disease resistance or susceptibility has not been observed on this hybrid.

What is claimed is:

1. A new and distinct variety of *Ipomoea* plant named 'Seki Blahrt,' substantially as illustrated and described herein.

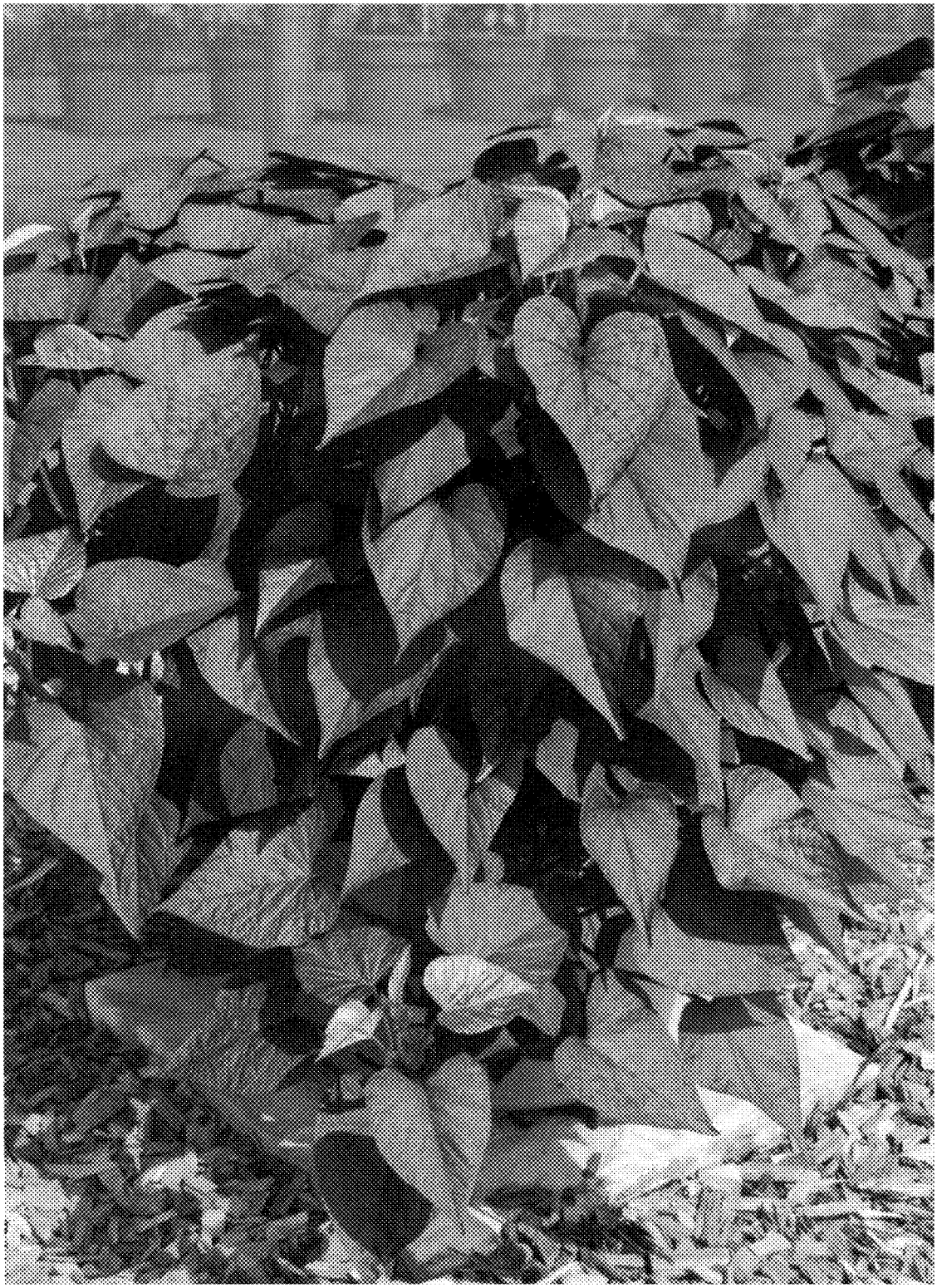

* * * * *